United States Patent
Haws

(10) Patent No.: US 9,888,981 B2
(45) Date of Patent: Feb. 13, 2018

(54) INTERDENTAL LATERALLY EXPANSIVE WEDGE

(71) Applicant: Larry Travis Haws, Centennial, CO (US)

(72) Inventor: Larry Travis Haws, Centennial, CO (US)

( * ) Notice: Subject to any disclaimer, the term of this patent is extended or adjusted under 35 U.S.C. 154(b) by 0 days.

(21) Appl. No.: 15/088,970

(22) Filed: Apr. 1, 2016

(65) Prior Publication Data

US 2017/0281310 A1    Oct. 5, 2017

(51) Int. Cl.
  *A61C 7/00*   (2006.01)
  *A61C 5/12*   (2006.01)
  *A61C 1/00*   (2006.01)
  *A61C 5/88*   (2017.01)

(52) U.S. Cl.
  CPC ............ *A61C 5/127* (2013.01); *A61C 1/0084* (2013.01); *A61C 5/88* (2017.02)

(58) Field of Classification Search
  CPC .......... A61C 5/127; A61C 1/0084; A61C 5/88
  See application file for complete search history.

(56) References Cited

U.S. PATENT DOCUMENTS

| | | |
|---|---|---|
| 3,781,994 A | 1/1974 | Hesselgren |
| 3,815,243 A | 6/1974 | Eames |
| 3,890,714 A | 6/1975 | Gores |
| 4,337,041 A | 6/1982 | Harsany |
| 5,037,392 A * | 8/1991 | Hillstead ................. A61F 2/958 604/916 |
| 5,507,646 A | 4/1996 | Roth |
| 5,527,181 A | 6/1996 | Rawls et al. |
| 5,573,400 A | 11/1996 | Asher |
| 5,664,946 A | 9/1997 | Bedi |
| 5,743,738 A | 4/1998 | Baffelli et al. |
| 5,890,901 A | 4/1999 | Fischer et al. |
| 6,007,334 A | 12/1999 | Suhonen |
| 6,013,055 A * | 1/2000 | Bampos ............ A61M 25/1002 604/103.07 |
| 6,042,380 A | 3/2000 | De Rowe |
| 6,074,210 A | 6/2000 | Garrison |
| 6,390,815 B1 * | 5/2002 | Pond .................... A61C 1/0061 433/100 |
| 6,439,886 B1 | 8/2002 | Thoreson |
| 7,284,982 B2 | 10/2007 | Brattesani |
| 7,331,788 B2 | 2/2008 | Kiilcher et al. |
| 8,011,924 B2 | 9/2011 | Kiilcher et al. |

(Continued)

*Primary Examiner* — Heidi M Eide
(74) *Attorney, Agent, or Firm* — Williams Intellectual Property; Benjamin F. Williams

(57) ABSTRACT

An interdental laterally expansive wedge includes a prismatic wedge member having a furled bottom side expansible from a first position to an expanded position when fluid is forcibly directed into the wedge member through a proximal interconnect. Lateral expansion of the wedge member is thereby effected when each of a pair of basal ridges is forced apart to impress consistent and even pressure in contact with interproximal structure, such as approximal teeth and a matrix band inserted to gird a cavosurface for approximal filling preparation and finishing. Importantly, the present interdental laterally expansive wedge is laterally expansive without effecting deformation or ballooning between and around the teeth, and prevents invasion into the cavity proper.

11 Claims, 3 Drawing Sheets

(56) References Cited

U.S. PATENT DOCUMENTS

| | | |
|---|---|---|
| 8,425,228 B2 | 4/2013 | McDonald |
| 9,333,102 B2 * | 5/2016 | Yachia ................... A61F 2/90 |
| 2002/0055084 A1 | 5/2002 | Fischer et al. |
| 2007/0112300 A1 * | 5/2007 | Roman ............. A61M 25/1002 |
| | | 604/103.07 |
| 2011/0171596 A1 * | 7/2011 | Clark ....................... A61C 5/88 |
| | | 433/149 |
| 2014/0277169 A1 * | 9/2014 | Hibri ................. A61B 17/7098 |
| | | 606/279 |

* cited by examiner

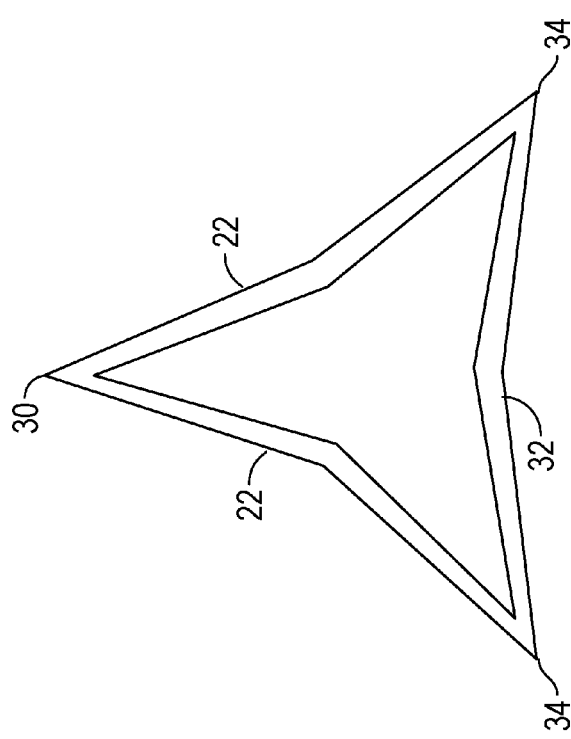
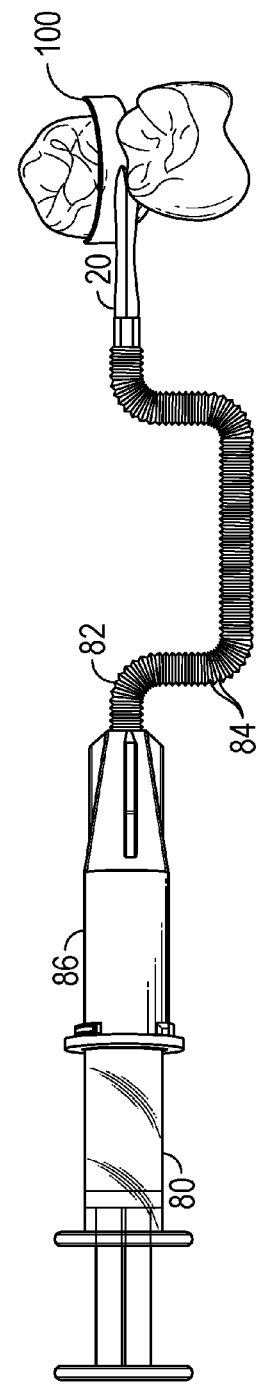
FIG. 4
FIG. 5

INTERDENTAL LATERALLY EXPANSIVE WEDGE

BACKGROUND OF THE INVENTION

Present practice in preparation and finishing of approximal fillings typically requires use of a matrix band to supportively gird a crown wherein the filling is to be performed. The matrix is tautly engaged in supporting contact with the tooth by means of a wedge fitted through the embrasures to marginally space approximal teeth apart and maintain pressure against a matrix there in situ.

Wedges seen in the current state of the art are typically solid, semi-rigid, polymeric elongate bodies that are manually forced between approximal teeth (for example, Eames, U.S. Pat. No. 3,815,243; Gores, U.S. Pat. No. 3,890,714; Harsany, U.S. Pat. No. 4,337,041; among others). While this method is effective, it does present certain issues. The wedge itself must be forcibly introduced through the embrasures to maintain position, and is essentially pressured in contact with an appropriately situated matrix band by virtue of its solid body forced between the teeth. Fitting of the wedge may be difficult, then, uncomfortable, and maintenance of the position problematic. Additionally, taut contact with the associated matrix band may likewise be variable, depending on which approximal teeth the wedge is fitted between and the variance of interdental and interproximal spaces evidenced between patients.

Traditional wedges also typically exhibit a constant gradient in cross-section wherein the width reduces consistently towards a tip. The narrowest portion of these wedges, then, is distally and endwise disposed. Position of such wedges through the interproximal space between approximal teeth, therefore, leaves a narrower portion of the wedge exposed in one embrasure versus the other, whereby pressure exerted by the wedge against an approximally fitted matrix band is thereby inconstant.

What is needed is an interdental laterally expansive wedge that is fittable in position between approximal teeth and thence expansible by introduction of a fluid compressibly forcible thereinto, to space apart a pair of basal ridges into consistent contact with neighboring teeth and any matrix band situated appropriately for approximal filling preparation and finishing. This lateral expansion is effective to maintain even and uniform contact with an approximal matrix band when a furled bottom side of the present interdental laterally expansive wedge is moved between a first position and an expanded position.

Inflatable wedge-like apparatuses are seen in the art, but present additional problems the instant invention is devised to overcome. For example, the interdental balloon taught by Suhonen (U.S. Pat. No. 6,007,334) is flexible and expansive, essentially a stretchable polymeric balloon that increases in volume simultaneously along all radii by act of inflation, whereby bulges and ballooning around sulcuses and embrasures present problems of deformation and application of inconsistent pressure between and around approximal teeth. Such ballooning may force the matrix band to intrude into the cavosurface into the cavity proper, and thus misalign a finished filling.

The inflatable dental device taught by Thoreson (U.S. Pat. No. 6,439,886) attempts to enable more lateral expansion, and even obviate use of a separate matrix band and wedge altogether. Thoreson teaches a plurality of flexible walls having fused inner areas by which introduction of fluid enables forcible expansion of at least one chamber to inflate the plurality of walls apart, thus effecting more lateral expansion. However, the flexibility Thoreson teaches enables deformation of the most exterior walls to intrude into the cavity, actually invading the cavosurface the band is meant to immure. This is particularly problematic when he device is used absent any matrix band, as Thoreson is given to teach.

The present invention, however, overcomes these and other problems by enabling an interdental laterally expansive wedge that includes a prismatic wedge having a non-expansive apical ridge disposed longitudinally between a distal tip and a proximal interconnect wherein forcible introduction of a fluid into the wedge effects expansion of a furled bottom side between a first position and an expanded position, whereby each of a pair of basal ridges is laterally separated apart around an angle of expansion delimited at the apical ridge, and even, uniform, and consistent pressure is applied to contacted surfaces without ballooning or appreciable deformation of the wedge into and around sulcluses or embrasures, and without invasion over the cavosurface within the interproximal space.

FIELD OF THE INVENTION

The present invention relates to an interdental laterally expansive wedge devised to effect application of consistent pressure against a matrix band without deformation within an interproximal space between a patient's teeth during approximal filling preparation and finishing. The interdental laterally expansive wedge includes a prismatic wedge member having a furled bottom side expansible from a first position to an expanded position when fluid is forcibly directed into the wedge member through a proximal interconnect, wherein lateral expansion of the wedge member is effected when each of a pair of basal ridges is forced apart to impress consistent and even pressure in contact with interproximal structure, such as approximal teeth and a matrix band inserted to gird a cavosurface for approximal filling preparation and finishing. Importantly, the present interdental laterally expansive wedge is thereby laterally expansive without effecting deformation or ballooning between and around the teeth, and prevents invasion of the cavity proper.

The present interdental laterally expansive wedge is further connectable to a flexible tube for use with an air syringe, when desired, whereby forcible introduction of fluid into the wedge is enabled distally relative the interproximal space wherein the wedge member is secured. Depressurization of the wedge member, and thus collapse of the furled bottom surface back to the first position is enabled by manual interaction with the air syringe, when used, or by depressurization effective at the proximal interconnect. The wedge is then more readily removable when the procedure has ended.

SUMMARY OF THE INVENTION

The present interdental laterally expansive wedge has been devised to offer improvements in the approximal filling arts. Present dental wedges and interdental balloons are either not inflatable at all, or if inflatable, devised to balloon flexible surfaces outward and thereby engender expansion. The flexibility of these devices' surfaces, as required to effect such ballooning and expansion, typically renders such interdental devices subject to deformation around teeth, ballooning within the embrasures while pinching in the interproximal space, whereby devices known in the prior art are not as effective at bounding a cavosurface or maintaining even pressure against a matrix band around a targeted tooth as may otherwise be effected by use of the present invention.

Taut, even pressure applied to maintain a matrix band bounding a cavosurface for approximal filling preparation and finishing is necessary to ensure the filling holds and conforms to the coronal surface of the tooth. Even small gaps, or uneven pressure applied against the matrix band, can lead to leakage and irregularities in filling preparation. Worse, ballooning of some inflatable wedges can buckle the matrix band, even if just incrementally, to invade into the cavity proper.

Non-inflatable wedges are fiddly, and sometimes difficult to install and remove. Moreover, the interproximal space between approximal teeth varies from mouth to mouth, and even within the same mouth, whereby non-expanding wedges cannot be universally applied.

The present device, then, has been devised to enable lateral expansion of a prismatic wedge member by forced pressurizing of a fluid thereinto, whereby a furled bottom surface is movable from a first position to an expanded position, and each of a pair of non-deformable medial side surfaces and each of a pair of basal ridges is thereby pressured to conjunct interproximal surfaces and structures without ballooning or deforming thereagainst. The present interdental laterally expansive wedge, therefore, enables position in any interproximal space for expansion to turgidly abut approximal teeth (and associated matrix band) to maintain consistent and even pressure thereagainst.

The present interdental laterally expansive wedge, therefore, includes a prismatic wedge member adapted for insertion into the interproximal space between approximal teeth. The wedge member is generally elongate and includes a distal tip, acuminate and rigid, and a proximal interconnect disposed to enable introduction of pressurized fluid into the wedge member.

An apical ridge is disposed longitudinally and apically upon the wedge member between the proximal interconnect and the apical tip. A furled bottom side is disposed underlying the apical ridge, said furled bottom side expansible between a first position and an expanded position when fluid is forced into the wedge member through the proximal interconnect, and the wedge member is thereby pressurized.

The prismatic wedge member is generally hourglass-shaped in longitudinal cross-section, with each of a pair of protuberances disposed on either side of a narrows. This hourglass shape is adapted to enable conformity to the interproximal space between approximal teeth and accommodate the gum line while enabling lateral expansion therein. The prismatic wedge member is generally triangular in transverse cross-section, with a hypocycloid perimeter when the furled bottom side is moved to the expanded position. Thus lateral expansion is effective when fluid is forcibly introduced into the wedge member and each of the pair of basal ridges is caused to separate apart, as the bottom side is moved to the expanded position. During lateral expansion, each of the pair of basal ridges travels through an angle of expansion delimited by the apical ridge. Thus the furled bottom side subtends a minimum angle when the furled bottom side is disposed in the first position and a maximum angle when said furled bottom side is disposed in the expanded position.

The proximal interconnect includes a non-expansive polygonal casing having a plurality of surfaces radially disposed thereabouts, whereby the proximal interconnect is purchasable for handling of the prismatic wedge member for position into an interproximal space. The proximal interconnect may include a unidirectional valve, or a releasable valve, whereby depressurization of the wedge member is enabled by interaction at the proximal interconnect.

The present interdental laterally expansive wedge is also connectable at the proximal interconnect to a flexible tube. The flexible tube includes a plurality of transverse corrugations whereby the flexible tube is bendable around a longitudinal axis for interconnection with an air syringe at an inlet housing disposed endwise thereupon. A user may, therefore, effect pressurization of the wedge member by action of the syringe compressing air (or other fluid) through the flexible tube to effect turgidity of the wedge member and deploy the furled bottom side to the expanded position. Pressure may be maintained in the wedge member by securement of the syringe plunger or by detachment of the flexible tube. Depressurization of the wedge member may be effected by manual action at the air syringe, when attached to the flexible tube and in fluid communication with the wedge member, or by action effected at the proximal interconnect proper, such as, for example, puncturing the polygonal casing or inserting some aciculate device to depress a valve release disposed endwise within the proximal interconnect.

For more convenient fit into the interproximal space between approximal teeth, the wedge member is compressible when the furled bottom side is in the first position, wherein the pair of basal ridges bounding the furled bottom side are each compressible closer together relative their position when the bottom side is in the first position. The wedge member thus enables compressibility when the bottom side is in the first position, whereby introduction of the wedge member into the interproximal space is more readily enabled and an elastic force is exerted to restore the bottom side towards the first position.

Once positioned, forcible introduction of fluid into the wedge member effects expansion of the furled bottom side to the expanded position, and each of the pair of basal ridges are pressed against interproximal structure and maintained in taut contact therewith. A matrix band thus disposed to gird a cavosurface upon a proximal tooth is thereby securely and supportively maintained conjunct the targeted tooth without forcibly intruding into the cavity proper as may otherwise occur with ballooning or other inflatable wedges.

Removal of the wedge is subsequently readily enabled by depressurization, whereby the bottom side is restored to the first position, and manual removal is thence effective from the interproximal space.

Thus has been broadly outlined the more important features of the present interdental laterally expansive wedge so that the detailed description thereof that follows may be better understood and in order that the present contribution to the art may be better appreciated.

Objects of the present interdental laterally expansive wedge, along with various novel features that characterize the invention are particularly pointed out in the claims forming a part of this disclosure. For better understanding of the interdental laterally expansive wedge, its operating advantages and specific objects attained by its uses, refer to the accompanying drawings and description.

BRIEF DESCRIPTION OF THE DRAWINGS

Figures

FIG. 4 is a transverse cross-section view of an example embodiment having a furled bottom side disposed in an expanded position.

FIG. 5 is an in-use view of an example embodiment interconnected with a flexible tube in open communication with an air syringe for pressurization and expansion of the furled bottom surface.

DETAILED DESCRIPTION OF THE DRAWINGS

Figure 1:
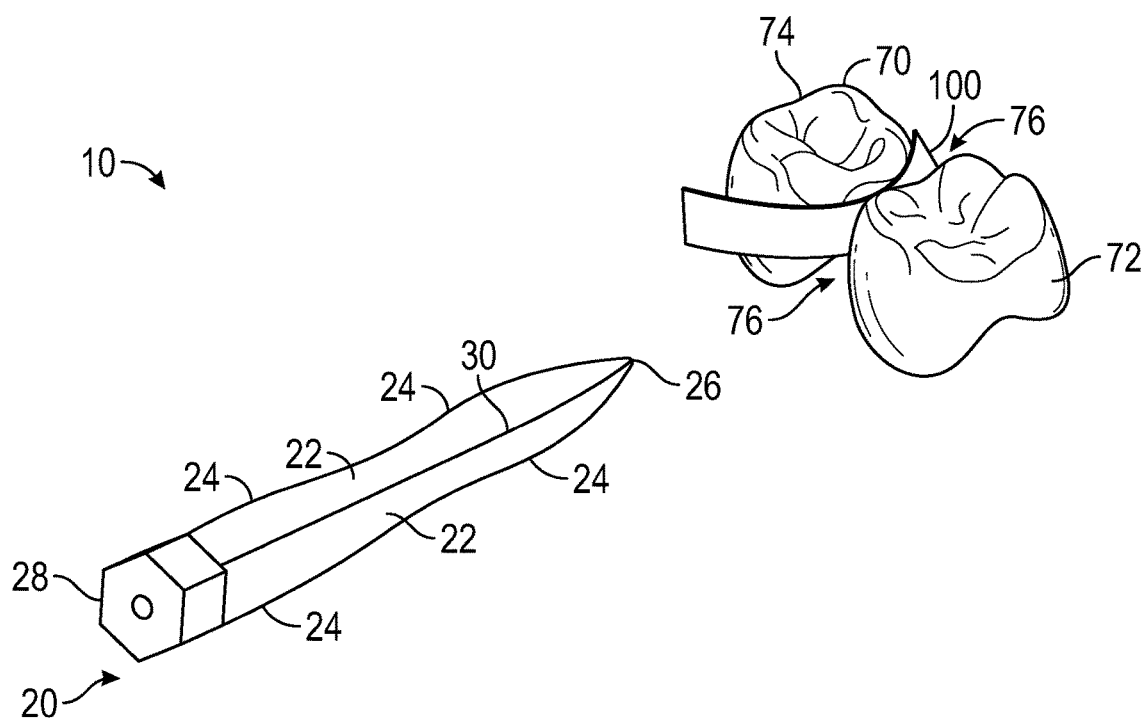
FIG. 1 is an isometric view of an example embodiment.
Figure 2:
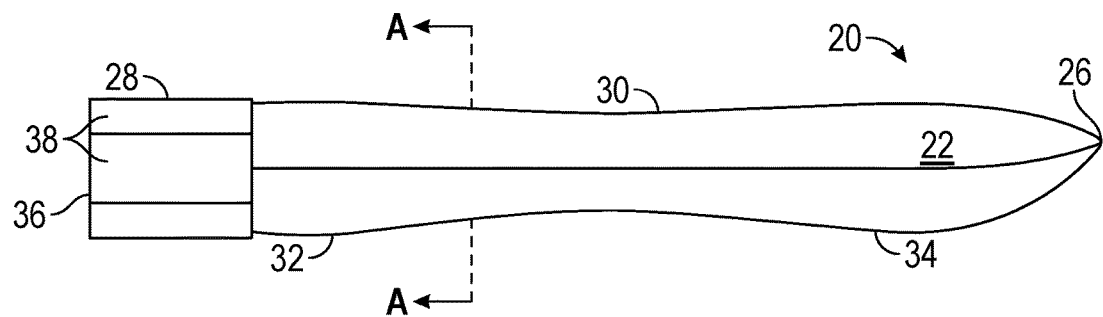
FIG. 2 is a side view of an example embodiment.
Figure 3:
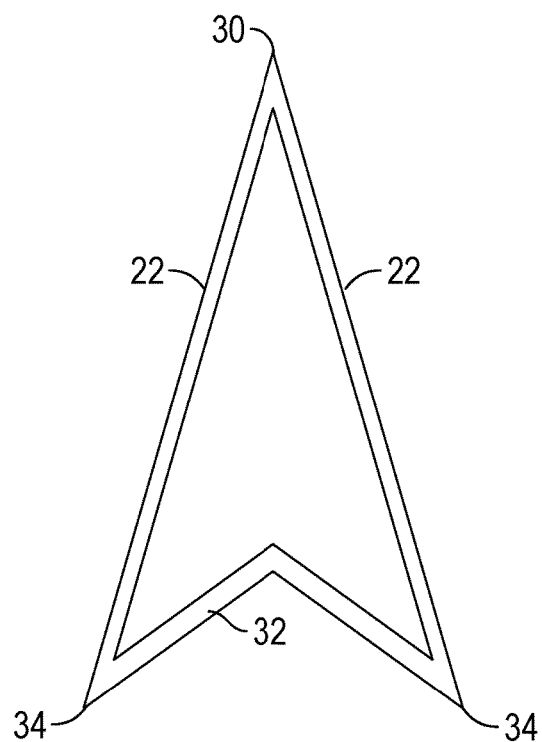
FIG. 3 is a transverse cross-section view of an example embodiment having a furled bottom side disposed in a first position.

With reference now to the drawings, and in particular FIGS. 1 through 5 thereof, example of the instant interdental laterally expansive wedge employing the principles and concepts of the present interdental laterally expansive wedge and generally designated by the reference number 10 will be described.

Referring to FIGS. 1 through 5 a preferred embodiment of the present interdental laterally expansive wedge 10 is illustrated.

The present interdental laterally expansive wedge 10 has been devised for insertion between adjacent teeth 70, 72, and there laterally expanded to maintain supporting contact with a matrix band 100 adjacently fitted to bound a cavosurface 74 during approximal cavity preparation and finishing. The term "lateral expansion", as used herein throughout, is taken to mean a forced separation of each of a pair of basal ridges 34 when a furled bottom side 32 is moved from a first position to an expanded position, each of said pair of basal ridges 34 expanding apart around an angle of expansion defined by an apical ridge and subtended by the bottom side 32, as will be described subsequently.

The present interdental laterally expansive wedge 10, therefore, includes a prismatic wedge member 20 devised for insertion into the buccal and lingual embrasures of approximal teeth. The term "prismatic", as used herein, is taken to include structure comprising an elongate body with a polygonal, obround, ovoid, or other transverse cross-section. In the embodiment shown in FIGS. 3 and 4, the prismatic wedge is shown with a generally triangular transverse cross-section, and with a hypocycloid perimeter when the furled bottom side 32 is disposed in the expanded position. In the embodiment shown in FIG. 2, the prismatic wedge member 20 comprises an hourglass shaped longitudinal cross-section whereby each of a pair of medial surfaces 22 having protuberances 24 is disposed to contact interproximal structures between approximal teeth 70, 72 (see for example FIG. 1).

The prismatic wedge member 20 includes a distal tip 26 endwise disposed thereupon. The distal tip 26 is acuminate to enable leading introduction into an embrasure 76. A proximal interconnect 28 is disposed on an opposite end of the wedge member 20, said proximal interconnect 28 enabling connection to means of introducing pressurized fluid into the wedge member 20 by which lateral expansion is effected. The proximal interconnect 28 may include a valve effective to selectively prevent bidirectional flow therethrough, whereby the prismatic wedge member 20 is capable to maintain pressure therein.

An non-expansive apical ridge 30 is disposed longitudinally and apically between the distal tip 26 and the proximal interconnect 28. A furled bottom side 32 is disposed underlying the apical ridge 30 and each of a pair of basal ridges 34 bound the furled bottom side 32 longitudinally disposed between the distal tip 26 and the proximal interconnect 28.

Fluid forcibly compressed into the wedge member 20 through the proximal interconnect 28, therefore, effects forced unfurling of the furled bottom side 32 between a first position and an expanded position and each of the pair of basal ridges 34 is thus forcible apart. Consistent, even contact of each basal ridge 34 and medial side surface 22 abutting neighboring teeth 70, 72 is thereby uniformly applied without ballooning of the wedge member 20, and an existing matrix band 100 is thereby uniformly maintained in taut supporting contact bounding a targeted cavosurface 74 without buckled intrusion into the cavity proper.

For fit through the embrasures 76 and position against the interproximal surfaces of adjacent teeth 70, 72, the prismatic wedge member 20 may also be laterally compressible when the furled bottom side 32 is disposed in the first position. Thus each of the pair of basal ridges 34 may be moveable in the first position closer together by compression of the wedge member 20, whereby an elastic force exerted by the furled bottom side 32 may enable some elastic rebound of the furled bottom side 32 towards the first position. It should be noted, however, that the compressibility of the wedge member 20 is effected by further compression of the furled bottom side 32 only, and not by any appreciable deformation of any of the wedge member 20 medial side surfaces 22 disposed in contact with any particular adjacent structure. The prismatic wedge member 20 is therefore compressibly fittable into an embrasure 76 and an elastic force is applied to approximal teeth 70, 72 previous to expansion of the wedge member 20. Subsequent expansion of the wedge member 20 thus increases force against interproximal surfaces between approximal teeth 70, 72.

In the embodiment illustrated, the proximal interconnect 28 includes a non-expansive polygonal casing 36. A plurality of surfaces 38 is radially disposed bounding the polygonal casing 36 whereby purchase for position of the wedge member 20 is enabled. The proximal interconnect 28 may be connectable to an air syringe 80 directly, or other pressurizing vessel, for forcible introduction of fluid (in this instance, air) into the wedge member 20 to effect movement of the furled bottom side 32 to the expanded position. Alternately, a flexible tube 82 is contemplated as connectable to the proximal interconnect 28. As shown in FIG. 5, this flexible tube 82 is contemplated to include a plurality of corrugations 84 and an inlet housing 86. The flexible tube 82 is positional in curved, bent, and sinusoidal array whereby the inlet housing 86 is more conveniently accessible away from the oral cavity of a patient. Connection to an air syringe 80 for forcible introduction of air into the proximal interconnect 28, to effect expansion of the furled bottom side 32 of the prismatic wedge member 20, is thus more readily enabled. In this embodiment, pressure is maintained within the wedge member 20 to maintain the expanded position by locking the plunger of the air syringe 80. Unlocking the plunger, or removing the syringe 80, thus enables depressurization and deflation of the wedge member 20.

Additional means of effecting depressurization of the wedge member 20 are contemplated as part of this invention 10, including, for example, manipulation of the proximal interconnect 28 to enable bidirectional airflow therethrough, such as, for example, exteriorly deforming the polygonal casing 36 or, alternately, effecting endwise puncture of the proximal interconnect 28, or interaction with a release valve as, for example, by depression with an available aciculate device.

What is claimed is:

1. An interdental laterally expansive wedge for insertion between adjacent teeth during approximal cavity preparation and finishing, said interdental laterally expansive wedge comprising:

a prismatic wedge member having:
   a distal tip;
   a proximal interconnect;
   an apical ridge disposed longitudinally and apically between the distal tip and the proximal interconnect;
   a furled bottom side; and
   a pair of basal ridges bounding the furled bottom side, each of said pair of basal ridges longitudinally disposed between the distal tip and the proximal interconnect;
wherein fluid forcibly compressed into the wedge member through the proximal interconnect effects forced deployment only of the furled bottom side between a first position and an expanded position to force each of the pair of basal ridges apart around an angle of expansion at the apical ridge and subtended by the bottom side whereby consistent, even contact of each basal ridge with adjacent teeth is uniformly applied and an existing matrix band is thereby uniformly maintained in taut supporting contact bounding a cavosurface in a targeted tooth without intrusion therein.

2. The interdental laterally expansive wedge of claim 1 wherein depressurization of the prismatic wedge member effects restoration of the furled bottom side to the first position.

3. The interdental laterally expansive wedge of claim 2 wherein the prismatic wedge member has a generally triangular transverse cross-section with a hypocycloid perimeter when the furled bottom side is disposed in the expanded position.

4. The interdental laterally expansive wedge of claim 3 wherein the prismatic wedge member is laterally compressible when the furled bottom side is disposed in the first position, whereby the prismatic wedge member is compressibly fittable into an embrasure between adjacent teeth and an elastic force is applied to interproximal surfaces of said adjacent teeth previous to movement of the furled bottom side to the expanded position.

5. The interdental laterally expansive wedge of claim 4 wherein the prismatic wedge member further comprises an hourglass shaped longitudinal cross-section.

6. The interdental laterally expansive wedge of claim 5 wherein the proximal interconnect includes a non-expansive polygonal casing.

7. The interdental laterally expansive wedge of claim 6 further comprising a flexible tube connectable to the proximal interconnect, said flexible tube comprising a plurality of corrugations and an inlet housing wherein the flexible tube is positional in curved, bent, and sinusoidal array and the inlet housing is connectable to an air syringe whereby air is forcibly compressible into the proximal interconnect to effect expansion of the furled bottom side of the prismatic wedge.

8. An interdental laterally expansive wedge for insertion between adjacent teeth during approximal cavity preparation and finishing, said interdental laterally expansive wedge comprising:
   a prismatic wedge member having an hourglass shaped longitudinal cross-section and a generally triangular transverse cross-section, said prismatic wedge member comprising:
      a distal tip;
      a proximal interconnect having a polygonal casing;
      an apical ridge disposed longitudinally and apically between the distal tip and the proximal interconnect;
      a furled bottom side moveable between a first position and an expanded position, said furled bottom side yet compressible when disposed in the first position and thereby compressible for fit between adjacent teeth;
      a pair of basal ridges bounding the furled bottom side, each of said pair of basal ridges longitudinally disposed between the distal tip and the proximal interconnect;
      a flexible tube sealably connectable at the proximal interconnect, said flexible tube having a plurality of corrugations transversely disposed thereupon; and
      an inlet housing disposed endwise upon the flexible tube, said inlet housing sealably connectable to an air syringe;
   wherein fluid is forcibly compressible into the wedge member through the flexible tube when connected at the proximal interconnect and expansion of the furled bottom side is thereby effective to force only each of the pair of basal ridges apart, whereby consistent, even contact of each basal ridge with adjacent teeth is uniformly applicable and an existing matrix band in appropriate position is thereby uniformly maintainable in taut supporting contact bounding a cavosurface without intrusion therein.

9. The interdental laterally expansive wedge of claim 8 wherein depressurization of the prismatic wedge member effects restoration of the furled bottom side to the first position.

10. The interdental laterally expansive wedge of claim 9 wherein said depressurization is effective by manual interaction with the air syringe.

11. The interdental laterally expansive wedge of claim 9 wherein said depressurization is effective by pressure exerted exteriorly upon the polygonal casing of the proximal interconnect.

* * * * *